United States Patent [19]
Aita et al.

[11] Patent Number: 6,156,031
[45] Date of Patent: Dec. 5, 2000

[54] TRANSMYOCARDIAL REVASCULARIZATION USING RADIOFREQUENCY ENERGY

[75] Inventors: Michael Aita, Shorewood, Wis.; Carl J. Simpson, Los Altos; Randy J. Kesten, Mountain View, both of Calif.

[73] Assignee: Eclipse Surgical Technologies, Sunnyvale, Calif.

[21] Appl. No.: 09/107,077

[22] Filed: Jun. 29, 1998

Related U.S. Application Data

[63] Continuation-in-part of application No. 08/942,874, Oct. 2, 1997, abandoned, and a continuation-in-part of application No. 08/968,184, Nov. 12, 1997, abandoned, which is a continuation of application No. 08/517,499, Aug. 9, 1995, abandoned.

[51] Int. Cl.[7] .................................................. A61B 18/04
[52] U.S. Cl. ................................ 606/33; 606/41; 606/45; 604/114
[58] Field of Search ................................ 606/33, 34, 37, 606/38, 41, 122; 604/114

[56] References Cited

U.S. PATENT DOCUMENTS

| | | |
|---|---|---|
| 4,211,230 | 7/1980 | Woltosz . |
| 4,682,596 | 7/1987 | Bales et al. . |
| 4,896,671 | 1/1990 | Cunningham et al. . |
| 5,056,517 | 10/1991 | Fenici . |
| 5,098,431 | 3/1992 | Rydell . |
| 5,104,393 | 4/1992 | Isner et al. . |
| 5,122,138 | 6/1992 | Manwaring . |
| 5,125,926 | 6/1992 | Rudco et al. .............................. 606/19 |
| 5,172,699 | 12/1992 | Svenson et al. . |
| 5,188,635 | 2/1993 | Radtke . |
| 5,197,963 | 3/1993 | Parins . |
| 5,215,103 | 6/1993 | Desai . |
| 5,222,501 | 6/1993 | Ideker et al. . |
| 5,230,349 | 7/1993 | Langberg . |
| 5,231,995 | 8/1993 | Desai . |
| 5,257,635 | 11/1993 | Langberg . |
| 5,281,213 | 1/1994 | Milder et al. . |
| 5,281,218 | 1/1994 | Imran . |
| 5,287,861 | 2/1994 | Wilk . |
| 5,295,484 | 3/1994 | Marcus et al. . |
| 5,334,193 | 8/1994 | Nardella . |
| 5,370,644 | 12/1994 | Langberg . |
| 5,385,148 | 1/1995 | Lesh et al. . |
| 5,389,096 | 2/1995 | Aita et al. . |
| 5,391,199 | 2/1995 | Ben-Haim . |
| 5,397,339 | 3/1995 | Desai . |

(List continued on next page.)

FOREIGN PATENT DOCUMENTS

| | | |
|---|---|---|
| 0 428 812 | 3/1995 | European Pat. Off. . |
| 0 797 956 | 10/1997 | European Pat. Off. . |
| WO 94/10904 | 5/1994 | WIPO . |
| WO 94/21165 | 9/1994 | WIPO . |
| WO 94/21167 | 9/1994 | WIPO . |
| WO 94/21168 | 9/1994 | WIPO . |
| WO 96/26675 | 9/1996 | WIPO . |

*Primary Examiner*—Linda C. M. Dvorak
*Assistant Examiner*—Roy Gibson
*Attorney, Agent, or Firm*—Heller, Ehrman, White & McAuliffe LLP

[57] ABSTRACT

The invention is directed to a system and method for revascularization of a patient's heart tissue by at least one burst of RF energy over an interval of about 1 to about 500 msec, preferably about 30 to about 130 msec. The device preferably has an elongated insulated, electrical conducting shaft with an uninsulated distal tip which is configured to emit RF energy. A method is described for myocardial revascularization of a human heart in which an elongated flexible device is used which includes a radiofrequency ablation device. In some embodiments, the device is configured to be introduced percutaneously, on other embodiments, the device is configured to be introduced intraoperatively. The RF energy emitter is advanced to a position adjacent a desired area of the heart wall. The device is activated, moving tissue to form a revascularization channel.

8 Claims, 7 Drawing Sheets

U.S. PATENT DOCUMENTS

| | | |
|---|---|---|
| 5,398,683 | 3/1995 | Edwards et al. . |
| 5,423,882 | 6/1995 | Jackman et al. . |
| 5,431,649 | 7/1995 | Mulier et al. . |
| 5,433,198 | 7/1995 | Desai . |
| 5,441,499 | 8/1995 | Fritzsch . |
| 5,443,489 | 8/1995 | Ben-Haim . |
| 5,476,495 | 12/1995 | Kordis et al. . |
| 5,480,422 | 1/1996 | Ben-Haim . |
| 5,487,757 | 1/1996 | Truckai et al. . |
| 5,492,119 | 2/1996 | Abrams . |
| 5,500,011 | 3/1996 | Desai . |
| 5,500,012 | 3/1996 | Brucker et al. . |
| 5,507,802 | 4/1996 | Imran . |
| 5,522,873 | 6/1996 | Jackman et al. . |
| 5,540,681 | 7/1996 | Strul et al. . |
| 5,545,200 | 8/1996 | West et al. . |
| 5,562,619 | 10/1996 | Mirachi et al. . |
| 5,571,088 | 11/1996 | Lennox et al. . |
| 5,573,533 | 11/1996 | Strul . |
| 5,575,772 | 11/1996 | Lennox . |
| 5,578,007 | 11/1996 | Imran . |
| 5,579,764 | 12/1996 | Goldreyer . |
| 5,591,159 | 1/1997 | Taheri . |
| 5,599,345 | 2/1997 | Edwards et al. . |
| 5,607,421 | 3/1997 | Jeevanandam et al. . |
| 5,607,462 | 3/1997 | Imran . |
| 5,609,151 | 3/1997 | Mulier et al. . |
| 5,620,439 | 4/1997 | Abela et al. . |
| 5,620,481 | 4/1997 | Desai et al. . |
| 5,626,575 | 5/1997 | Crenner . |
| 5,636,634 | 6/1997 | Kordis et al. . |
| 5,637,090 | 6/1997 | McGee et al. . |
| 5,657,755 | 8/1997 | Desai . |
| 5,658,278 | 8/1997 | Imran et al. . |
| 5,662,124 | 9/1997 | Wilk . |
| 5,672,170 | 9/1997 | Cho et al. . |
| 5,683,366 | 11/1997 | Eggers et al. . |
| 5,697,882 | 12/1997 | Eggers et al. . |
| 5,722,975 | 3/1998 | Edwards et al. . |
| 5,725,523 | 3/1998 | Mueller . |
| 5,725,524 | 3/1998 | Mulier et al. . |
| 5,728,144 | 3/1998 | Edwards et al. . |
| 5,741,249 | 4/1998 | Moss et al. . |
| 5,743,903 | 4/1998 | Stern et al. . |
| 5,755,714 | 5/1998 | Murphy-Chutorian . |
| 5,769,843 | 6/1998 | Abela et al. . |
| 5,785,059 | 7/1998 | Tacker, Jr. . |
| 5,843,019 | 12/1998 | Eggers et al. ............................ 604/22 |

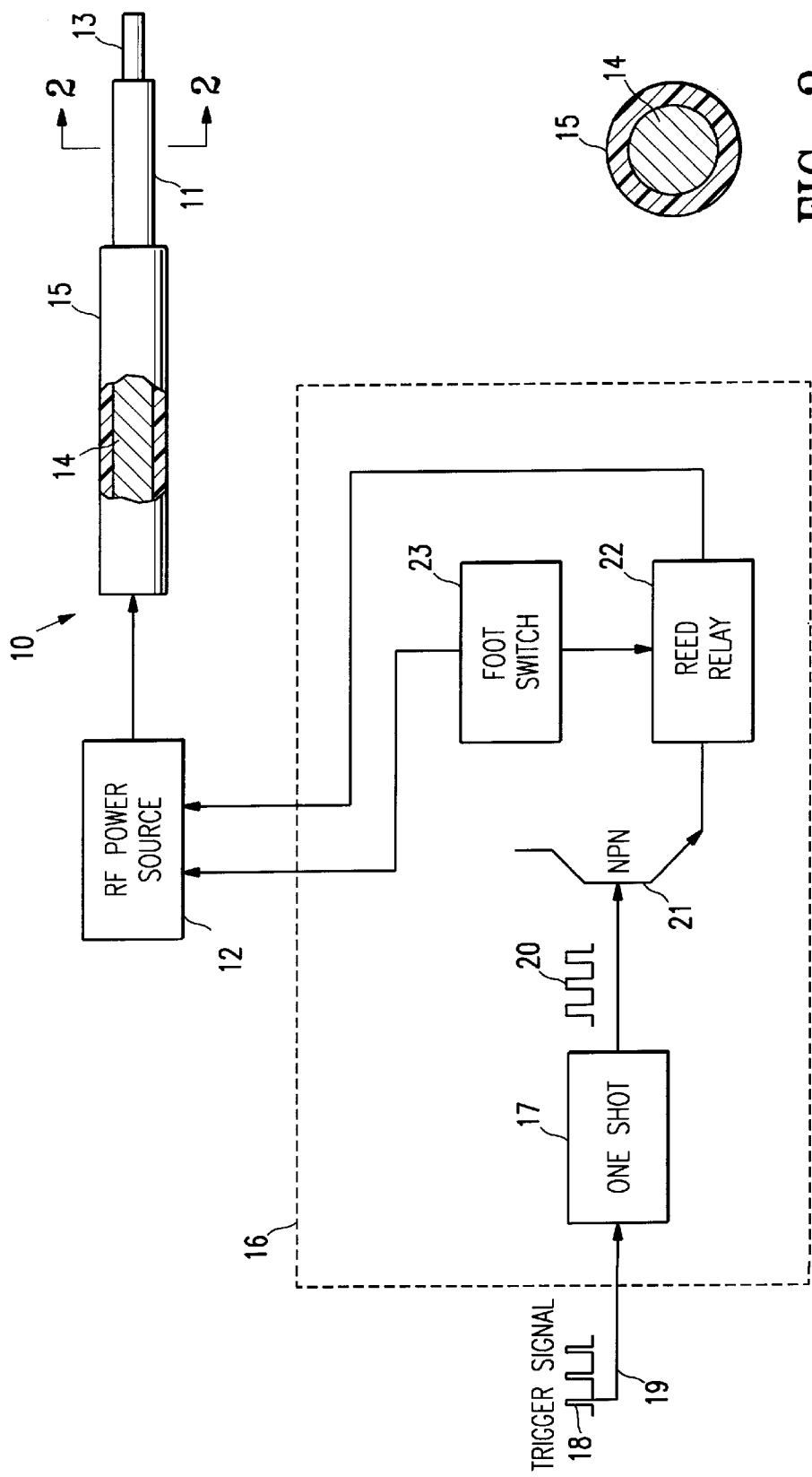

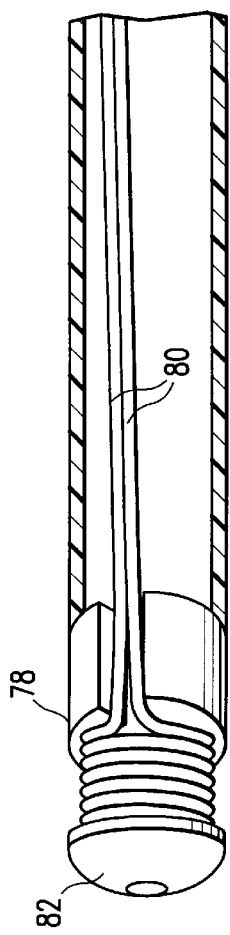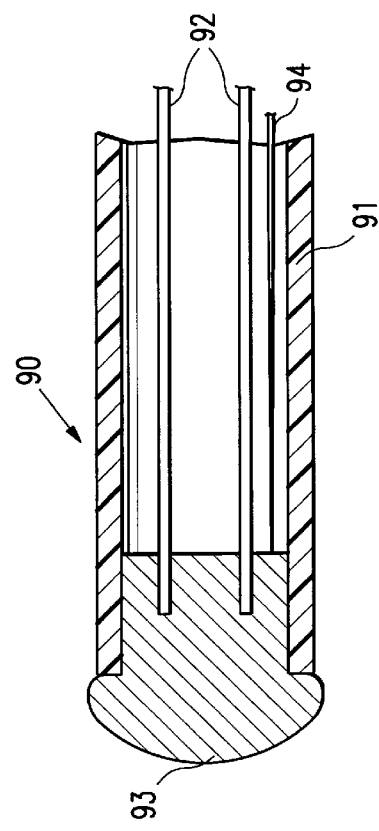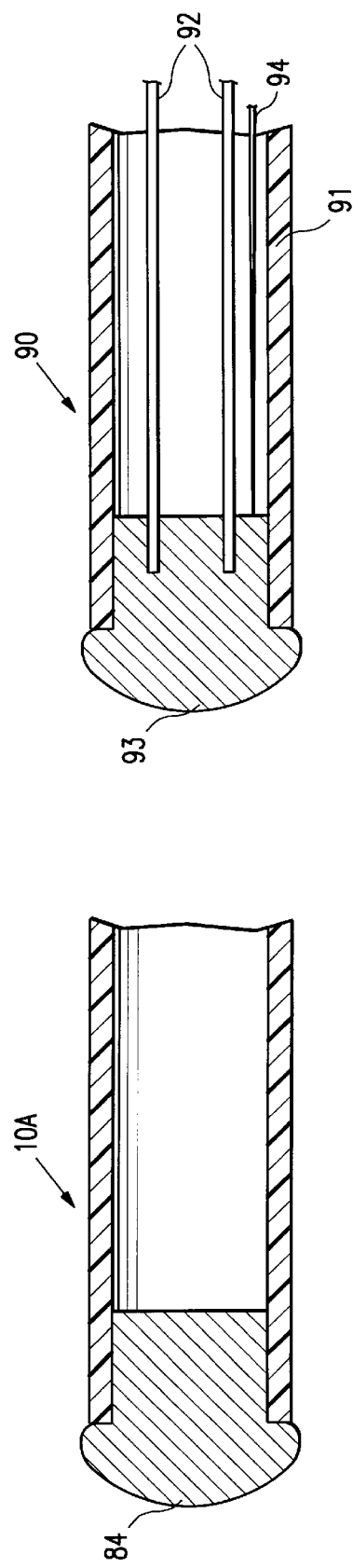
FIG. 8
FIG. 9
FIG. 10

TRANSMYOCARDIAL REVASCULARIZATION USING RADIOFREQUENCY ENERGY

RELATED APPLICATIONS

This application is a continuation-in-part of application Ser. No. 08/942,874, filed Oct. 2, 1997 abandoned, and application Ser. No. 08/968,184, filed Nov. 12, 1997 abandoned, which are both continuations of application Ser. No. 08/517,499, filed Aug. 9, 1995 abandoned. All of the above-referenced applications are hereby incorporated by reference in their entirety. This application also claims priority from co-pending application Ser. No. 08/847,290 filed Oct. 7, 1997.

BACKGROUND OF THE INVENTION

This invention is directed to the ablation or disruption of tissue in the wall of a patient's heart and particularly to form channels within the heart wall in order to perform transmyocardial revascularization (TMR), to deliver therapeutic or diagnostic agents to various locations in the patient's heart wall or for a variety of other utilities.

As presently used, TMR involves forming a plurality of channels in a ventricular wall of a patient's heart by means of laser energy. The first clinical trials of the TMR procedure using laser energy were performed by Mirhoseini et al. See for example the discussions in Lasers in General Surgery (Williams & Wilkins; 1989), pp. 216–223. Other early disclosures of the TMR procedure are found in an article by Okada et al. in Kobe J. Med. Sci 32, 151–161, October 1986 and in U.S. Pat. No. 4,658,817 (Hardy). These early references describe intraoperative TMR procedures which require an opening in the chest wall and include formation of channels completely through the heart wall starting from the epicardium.

U.S. Pat. No. 5,554,152 which issued on Dec. 20, 1994 (Aita et al.), which is incorporated herein in its entirety, describes a system for TMR which is introduced through the chest wall either as an intraoperative procedure where the chest is opened up or as a minimally invasive procedure where the system is introduced into the patient's chest cavity through small openings in the chest by means of a thoroscope.

In U.S. Pat. No. 5,389,096 (Aita et al.) a percutaneous TMR procedure is described wherein an elongated flexible laser based optical fiber device is introduced through the patient's peripheral arterial system, e.g., the femoral artery, and advanced through the aorta until the distal end of the device extends into the patient's left ventricle. Within the left ventricle, the distal end of the optical fiber device is directed toward a desired location on the patient's endocardium and urged against the endocardial surface while a laser beam is emitted from its distal end to form the channel.

Copending application Ser. No. 08/078,443, filed on Jun. 15, 1993 (Aita et al.), which is incorporated herein in its entirety, describes an intravascular system for myocardial revascularization which is percutaneously introduced and advanced into the left ventricle of the patient's heart where laser energy initiates revascularization through the endocardium and into the myocardium. This procedure eliminates the need of the prior procedures to open the chest cavity and to penetrate the epicardium in order to form the channel through the endocardium into the myocardium.

The laser based revascularization procedure has been shown to be clinically beneficial to a variety of patients, particularly patients who were, for the most part, not suitable candidates for by-pass surgery or for minimally invasive procedures such as angioplasty or atherectomy. However, to date the equipment for laser based systems has been quite expensive. What has been needed is a system which is less expensive than but as clinically effective as laser based systems. The present invention satisfies these and other needs.

SUMMARY OF THE INVENTION

The present invention is directed to a method and system for the revascularization of a region of a patient's heart by ablating or disrupting tissue in said region with emissions of radiofrequency (RF) energy and is particularly directed to the methods and systems to ablate or disrupt tissue in the patient's heart wall to form channels therein by means of such RF energy.

One method includes the step of inserting an elongated shaft having an RF energy emitter into a patient's vasculature. Preferably, a system for guiding the device is also provided. The RF energy emitter is guided to the interior of the left ventricle and positioned against a desired portion of the ventricle's inner wall. Then, the RF energy emitter is activated to remove or otherwise injure tissue. The RF energy emitter may be advanced so as to remove tissue until a channel or disrupted area is formed to the desired depth. Methods for controlling the depth of channel formation include fluoroscopic or ultrasonic visualization or advancing the revascularization means a fixed distance. In addition, penetration limitation can be achieved with mechanical penetration limiters such as those taught in copending U.S. application Ser. No. 08/486,978 now U.S. Pat. No. 5,951,541, which is hereby incorporated by reference in its entirety. The RF energy emitter is repositioned against another portion of the heart wall and the process is repeated until enough channels or regions of ablated tissue are formed to provide the desired revascularization.

In accordance with one embodiment of the invention, tissue is ablated within a patient's heart wall by means of one or more bursts of RF emissions over intervals of about one to about 500 msec and preferably about 30 to about 130 msec. A radiofrequency burst may comprise a continuous emission or discontinuous emission, i.e. be pulsatile, and, if pulsatile, may involve a plurality or train of pulses which may or may not be of the same width (duration), frequency or amplitude.

The RF emissions are preferably controlled so that heart tissue is exposed to the RF energy over a desired period and particularly over a period which will avoid interfering with the patient's heart beat, e.g., just after the R wave but before the T wave. One to about 10 bursts of RF energy may be required to effectively form the desired channel within the patient's heart wall and preferably one burst of RF emission is delivered per heart cycle. The RF energy source generally should have a peak power output of about 150 to about 500 watts, preferably about 200 to about 300 watts.

It also may be desirable to operate the RF energy emitter at more than one energy level. Initially, the channel formation or tissue disruption may be performed at a relatively high energy level to position and anchor the RF ablation device. For greater control, the remainder of the procedure may be performed at a lower energy level.

One presently preferred system for revascularizing a patient's heart wall includes an RF energy transmitting member which has a proximal end, and an uninsulated distal tip configured to emit RF energy. The system is introduced into the patient and advanced within the patient until the uninsulated distal tip thereof is disposed adjacent to a surface of the patient's heart wall. At least one burst of RF energy from an RF energy source is transmitted through the RF energy transmitting member to the uninsulated distal tip thereof. The RF energy is then emitted from the distal tip and into the heart wall in contact with said distal tip. In preferred embodiments, the channel formed in the heart wall preferably has an aspect ratio, i.e., depth to width, of at least 1, preferably at least 2.

Any particles of tissue produced by the RF energy emitter have the potential to create emboli if allowed to escape into the patient's circulatory system. Accordingly, in a number of these embodiments, the RF energy emitter includes lumens for perfusion and aspiration to remove the particles from the patient's body. Alternatively, the RF energy emitter is configured to produce particles small enough to safely propagate through the smallest branches of the patient's vasculature, approximately 6–10 μm in diameter.

One embodiment of the invention utilizes a percutaneous approach in which a flexible RF energy emitter is advanced through the patient's vasculature until a distal portion of the system enters a heart chamber such as the left ventricle. The RF energy transmitting member is advanced so that the uninsulated distal tip which emits RF energy contacts the interior surface of the heart wall which defines in part the heart chamber. At least one burst of RF energy is emitted from the uninsulated distal tip of the system into the patient's heart wall wherein tissue is ablated or otherwise disrupted, resulting in the revascularization of the heart wall region.

Another embodiment of the invention involves a minimally invasive approach where a small incision is made in the patient's chest and with or without the benefit of a trocar sheath, an elongated RF energy transmitting member is advanced into the patient's chest cavity until the uninsulated distal tip of the RF transmitting member contacts the exterior of the patient's heart. One or more bursts of RF energy are emitted from the uninsulated distal tip so as to ablate or disrupt tissue within the patient's heart wall causing the revascularization thereof, as in the previously discussed embodiments of the invention. A similar procedure may be used in conjunction with an open chest procedure such as coronary by-pass surgery or in other surgical procedures, as is the case with laser based transmyocardial revascularization.

The RF energy emitter preferably includes an RF energy transmitting member which is insulated along its length except for the distal tip thereof which is uninsulated and which is configured to contact the surface of the heart wall and to emit bursts of RF energy therefrom into adjacent tissue of the heart wall. The uninsulated distal tip can have a diameter of about 0.025 to about 0.2 inch (0.64–5.1 mm), preferably about 0.04 to about 0.08 inch (1–2 mm) and a length of about 0.1 to about 5 mm, preferably about 1.5 to about 3.5 mm. The distal tip may be solid or hollow and may be relatively sharp or blunt. However, it should not be sharp enough to penetrate the tissue of the heart wall when pressed against the wall to maintain contact during the emission of RF energy bursts. The average power level should be about 50 to about 500 watts, preferably about 100 to about 300 watts. The frequency of the RF current should not be less than 100 kHz and preferably is about 250 to about 500 kHz.

The method and system of the invention effectively ablates or disturbs tissue within the patient's heart wall to revascularize the ablated region and particularly can be used to form channels within the heart wall. These and other advantages of the invention will become more apparent from the following detailed description of the invention and the accompanying exemplary drawings.

BRIEF DESCRIPTION OF THE DRAWINGS

FIG. 1 is a schematic illustration of a system for revascularizing heart tissue which embodies features of the invention.

FIG. 2 is a transverse cross-section of the RF energy transmitting member of the system shown in FIG. 1 taken along the lines 2—2.

FIGS. 8 and 9 are schematic longitudinal cross-sectional views of RF systems useful in the practice of this invention.

FIG. 10 is a schematic longitudinal cross-sectional view of a thermal energy ablation means useful in the practice of the invention.

DETAILED DESCRIPTION OF THE DRAWINGS

Figure 3:
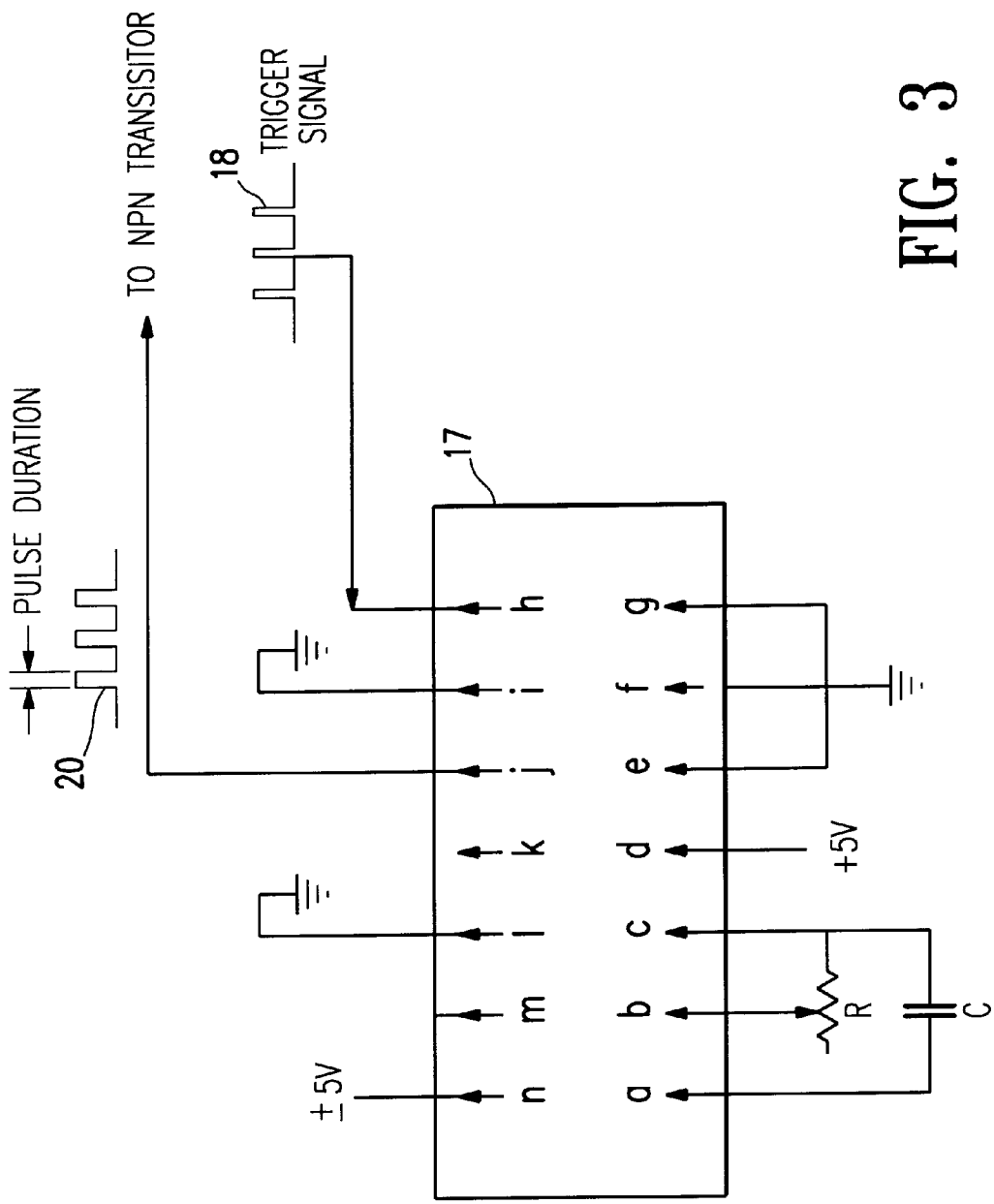
FIG. 3 is a schematic illustration of the one shot shown in FIG. 1.

FIGS. 1 and 2 depict an RF system 10 embodying features of the invention which includes an RF energy transmitting member 11 having a proximal end configured for electrical connection to a source 12 of RF energy and an uninsulated exposed distal end 13 which is configured to emit pulsed RF energy received from the source and transmitted through the RF energy transmitting member. The RF energy transmitting member 11 includes an electrical conductor 14 which may be hollow or solid, a single or multiple strand and an insulating jacket 15 formed of suitable insulating polymeric material. A suitable source of RF energy is the Excaliber RF Generator from Aspen Laboratories (ConMed, Englewood, Colo., USA).

The output from the RF energy source 12 is pulsed by pulse-trigger system 16 which includes a one-shot 17, such as CD4047 sold by National Semiconductor, configured to receive trigger signals 18 through electrical conductor 19 and generate in response a pulsed output signal 20 connected to a NPN transistor 21. The pulsed output signal 20 from the one-shot 17 actuates the transistor 21 for the duration of the output signal. The output of the transistor 21 is connected to reed relay 22 which is configured to close upon receiving the output from the transistor 21. The output of the reed relay 22 is connected in series to the foot switch 23. When the foot switch 23 is closed and reed relay 22 is closed, the RF energy source is actuated to emit RF energy for the duration of the output of the reed relay 22.

FIG. 3 illustrates in more detail the one-shot shown in FIG. 1 which has 14 pins, identified as pins a–n in FIG. 3. The one-shot shown in FIG. 3 has the pins designated with letters a–n to avoid confusion with other reference numbers used herein. The one-shot model number CD4047 has these pins numbered 1–14. The trigger signal 18 from an ECG unit is received by pin h and upon receipt of the trigger signal an on signal is emitted from pin j. The duration of the on signal from pin j is controlled by the resistance R and capacitance C from the RC circuit connected to pins a–c as shown. The resistance R can typically range from about 0.1 to about 1 meg ohm and the capacitance can typically range from about 0.08 to about 0.12 microfarads to control the duration of the pulses of output signal 20 from about 50 to about 300 msec.

Figure 4:
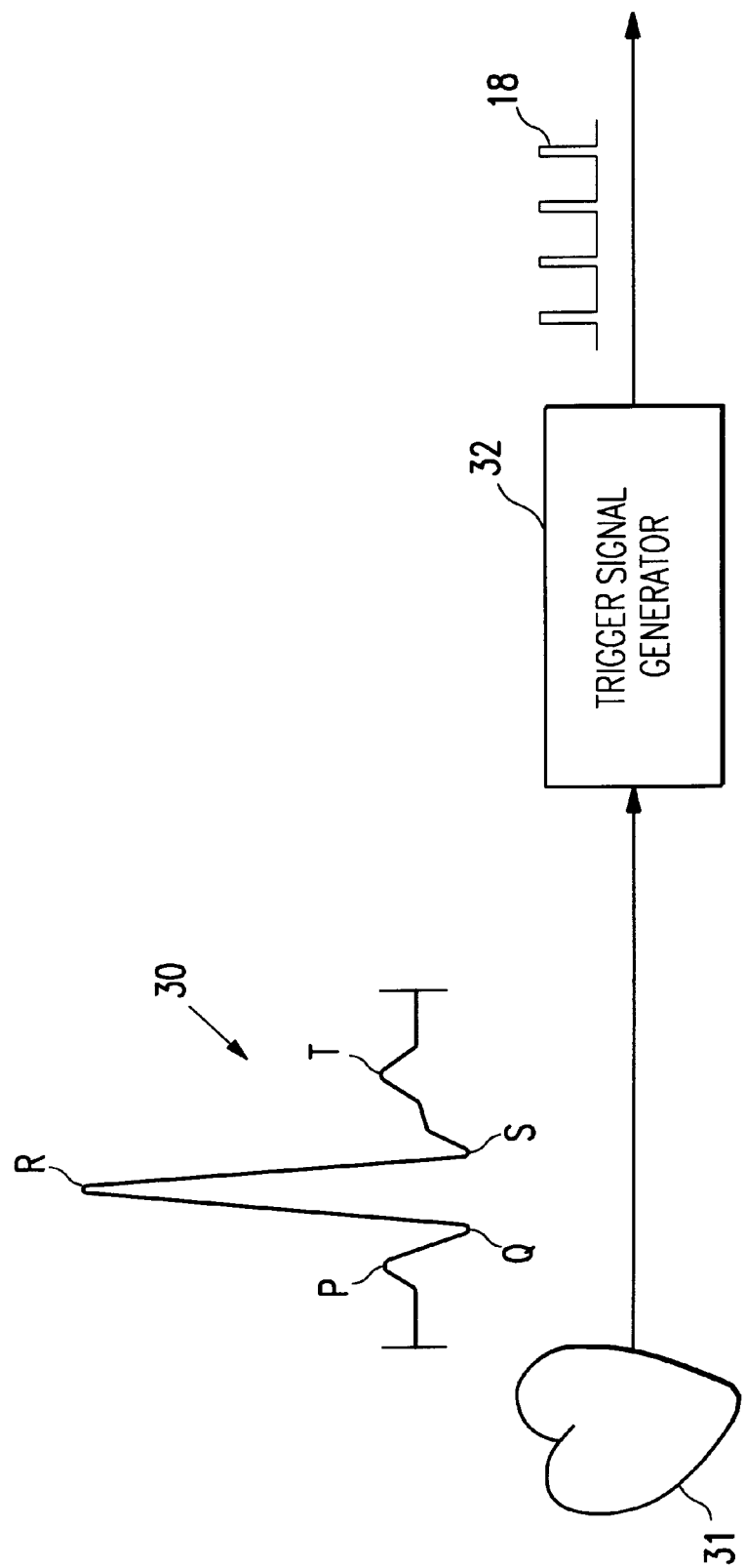
FIG. 4 is a schematic illustration of a system for generating trigger signals based upon the patient's heart beat.

FIG. 4 schematically illustrates a system of generating trigger signals 18 based upon the patient's heart cycle 30. The signals from the patient's heart 31 are detected with a conventional ECG unit and the detected signals are transmitted to a trigger generating system 32 which may also be contained in the ECG unit. The trigger signal generating system 32 is preprogrammed to emit one or more trigger signals 18 at a predetermined time between the R and the T wave of the heart cycle 30.

Figure 5:
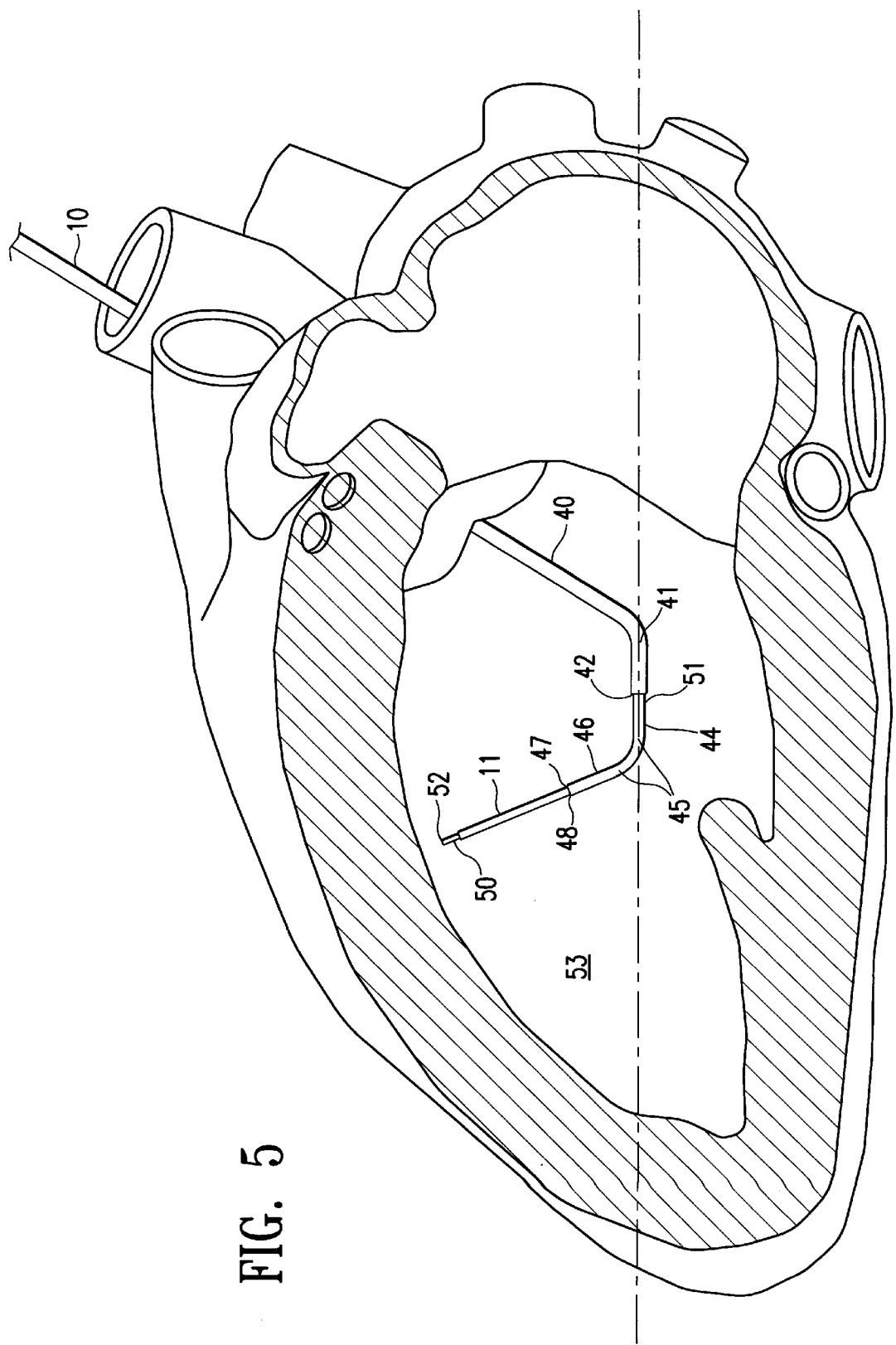
FIG. 5 is an elevational view of a delivery system for the RF energy emitter for positioning the operative distal end thereof adjacent to the endocardium of a patient's heart wall.

Reference is made to FIG. 5 which illustrates a system for the percutaneous delivery of an RF system which has an outer catheter 40, a shaped distal end 41, a port 42 in the distal end of the outer catheter and an inner lumen extending within the outer catheter to the port in the distal end. This system also includes an inner catheter 44 which is slidably and rotatably disposed within the inner lumen of the outer catheter 40 and which has a shaped distal section 45, a distal end 46, a port 47 in the distal end of the inner catheter and an inner lumen 48 extending therein to the port in the distal end. An RF energy emitter 50 is slidably disposed within the inner lumen of inner catheter 44. The distal section 45 of the inner catheter 44 is at an angle with respect to the main shaft section 51 of the inner catheter to orient the RF energy emitter 50 extending out the distal end of the inner catheter. In this manner the disposition of the distal end 52 of the RF energy emitter 50 can be controlled by raising and lowering and rotation of the RF energy emitter within the inner lumen of the inner catheter 44 and the inner catheter within the inner lumen of the outer catheter 40. The distal end 52 of the RF energy emitter 50 is thus pointed in a desired direction to the endocardium defining the left ventricle 53. Longitudinal and rotational movement of the inner catheter 44 provides access to a large region of the endocardium.

Figure 6:
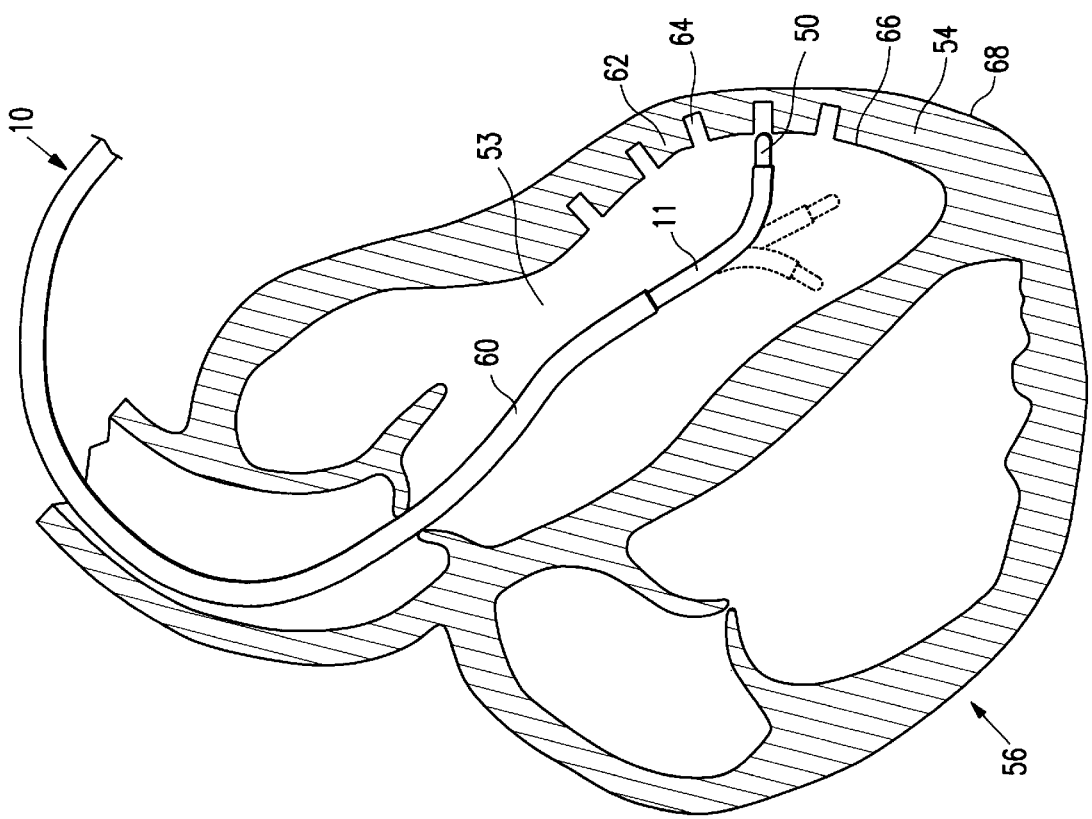
FIG. 6 is a schematic elevational view, partially in cross-section, of a human heart showing revascularization of the myocardium according to the invention.

Referring to FIG. 6, the present invention also comprises a method for revascularizing the myocardium 54 of a human heart 56. An RF system 10 including an elongated shaft 60 with an RF energy emitter 50 disposed at the distal end is inserted into the vasculature of a patient, generally through one of the major vessels by the conventional Seldinger technique. The RF energy emitter 50 is advanced into the left ventricle 53 and positioned against a desired portion of the heart muscle 62 in need of increased blood circulation due to cardiovascular disease. The RF energy emitter 50 is activated and urged against the muscle 62 to effect removal of tissue, forming the revascularization channel 64. The tissue region disturbed or ablated should extend a desired distance through the endocardium 66 and into the myocardium 54 without perforating the epicardium 68. The RF energy emitter 50 is deactivated, withdrawn from channel 64 and repositioned against another portion of muscle 62.

In another method of the invention (not shown) an RF system 10 having an RF energy emitter 50 on the distal end is introduced through a small opening in the patient's chest wall. RF system 10 is advanced until the RF energy emitter 50 is positioned against the ischemic portion of the heart muscle 62. The RF energy emitter 50 is activated and urged towards the muscle 62. Tissue is removed sequentially from the epicardium 68, the myocardium 54 and the endocardium 66 to form the revascularization channel 64 into the left ventricle 53. As above, the RF energy emitter 50 is then deactivated, withdrawn from the muscle 62 and repositioned. In either method, the operator repeats the process until a sufficient number of channels 64 or similar revascularization sites are formed in muscle 62 to treat the ischemic condition.

In operation, the RF energy emitter 50 may be maintained in position on the heart muscle 62 by a controlled advance and gentle pressure, to insure that the RF energy emitter 50 is not dislodged during formation of the channel. Alternatively, the RF energy emitter 50 can be maintained in place by applying a vacuum at the distal tip thereof.

In embodiments where the RF energy emitter 50 allows rapid, intermittent switching between active and inactive states, the operation may be synchronized with the patient's heart cycle to avoid channel formation during the vulnerable period of the heart cycle. Preferably, the RF energy emitter 50 is subject to automatic control means which prevents operation during the T-wave portion of the ECG, as known in the art.

Additionally, the RF energy emitter 50 may operate at two or more energy levels. Preferably, the initial tissue removal to penetrate the endocardium 66 is performed at a relatively high energy level. The rapid channel formation at this energy level helps anchor the RF energy emitter 50 within the channel 64. The remainder of the tissue removal may be performed at a lower energy level to provide slower channel formation and greater control.

Figure 7:
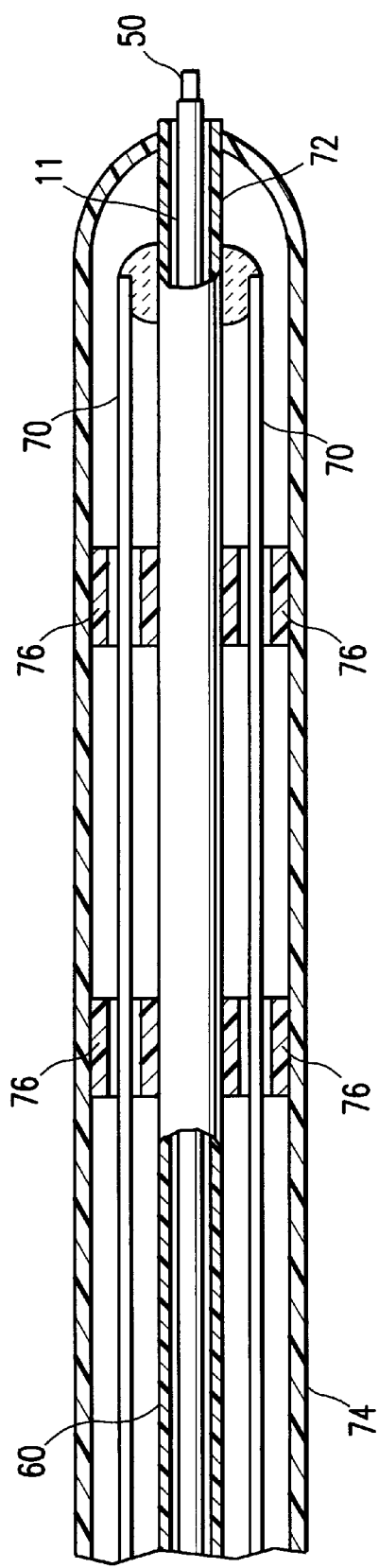
FIG. 7 is a schematic longitudinal cross-sectional view of the distal portion of a deflectable elongated RF system which embodies features of the invention.

In the embodiment depicted in FIG. 7, a plurality of control lines 70 are connected at their distal ends to the distal end 72 of shaft 60 such as by adhesive bonding. Adhesive bonding may utilize any of a variety of adhesives, including cyanoacrylate. At least two, and preferably four, control lines 70 are thus axially, and preferably symmetrically, disposed about shaft 60. Axial movement of control lines 70 will thus change the angle of deflection of distal end 72 of shaft 60 with respect to its proximal end. A mechanism (not shown) such as a ring or knob may be attached to the proximal ends of control lines 70 to allow manipulation of control lines 70. Control lines 70 are preferably approximately 3-mil stainless steel wire, but may be similar filaments, such as nylon, or other suitable materials having appropriate tensile strength.

In addition, an outer tubular member 74 preferably encloses control lines 70 and shaft 60, forming a protective covering. Outer tubular member 74 is secured at its distal end to distal end 72 of shaft 60, rearward of RF energy emitter 50. In order to facilitate precise control of the tip during the procedure, control lines 70 are routed through spaced apart channels 76 that are attached to the outer surface of shaft 60. Channels 76 are preferably constructed of 30 gauge polyamide tubing. Control lines 70 are thus guided to remain both separated and within well controlled areas on the exterior of shaft 60, thus allowing for the accurate guidance of the RF system 10 through the remote manipulation of control lines 70.

Another means for guiding shaft 60 and RF energy emitter 50 into a proper position within the heart is to place the shaft 60 within a deflectable guiding catheter having dual axis steerability, for an added degree of steerability and control. Co-pending application, Ser. No. 08/438,743 filed May 10, 1995, entitled DELIVERY SYSTEM AND METHOD FOR MYOCARDIAL REVASCULARIZATION discloses such a system and is hereby incorporated in its entirety by reference thereto. In practice, the positioning of the device may be viewed by esophageal ultrasound imaging, trans-thoracic ultrasound imaging and trans-thoracic fluoroscopic imaging. Accordingly, it may be desirable to add one or more radiopaque marker bands to the distal end 72 of shaft 60, for fluoroscopic imaging. RF energy emitter 50 may thereby be aimed and controlled for forming channels 64 in the myocardium 54 of the ischemic heart muscle 62.

Alternative means of ablation are suitable, including thermal and other radiation means. For example, FIG. 8 illustrates the distal portion of an RF system 100 which has a thermal ablator 78. The thermal ablator 78 has an electrode 80 wrapped around thermally-conductive probe 82 and extending the length of the system 100. The diameter of probe 82 should be from about 1.0 to 5.0 mm. The proximal ends of the electrode 80 are connected to a radiofrequency generating means (not shown). Applying radiofrequency energy at suitable frequency and power through electrode 80 produces resistive heating transmitted through probe 82. Generally, energy from about 30 MHz to about 10 GHz is suitable to generate sufficient heat at probe 82 to ablate heart tissue.

Radiofrequency energy may also provide inductive heating as shown in FIG. 9. The distal portion of an RF system 10a has a ferrite probe 84 on the end. A radiofrequency generating means (not shown) irradiates the patient's body with energy at a frequency to which body tissue is relatively transparent but the ferrite probe readily absorbs, generating ablating heat.

EXAMPLE

Eighteen channels were made in the heart of a live, anesthetized medium size dog by means of pulsed RF energy. The wattage and the size and type of distal tip of the RF delivery system were varied to determine the nature of the channels formed which result from such variations. The results are set forth in the table below.

ablating the heart tissue. The probe 93 should generally be about 0.1 to 5.0 mm in diameter. The thermal probe 93 should heat to between about 60 degrees centigrade to about 600 degrees centigrade. The device may also comprise a sensing electrode 94 to monitor the temperature of the thermal probe 93. Such a device can be used in a method of forming a revascularization channel in a desired region of a wall of a patient's heart, the wall having an inner endocardium layer, an outer epicardium layer and an intermediate myocardium layer between the endocardium and the epicardium layers. The device, having proximal and distal ends and a means to form a revascularization channel comprising radiofrequency ablation means located on the distal end is introduced into the body of a patient. The distal end of the device is directed to the desired region of the wall wherein the revascularization channel is to be formed, and radiofrequency energy is supplied to the radiofrequency ablation means to form a revascularization channel in the myocardium layer. In addition, the radiofrequency ablation means can be a probe connected to a first and second electrode which extend the length of the device. Radiofrequency energy can can then be supplied across the electrodes to form a revascularization channel.

Those skilled in the art will recognize that various changes can be made to the invention without departing from the scope thereof. There has been described herein various systems and methods for myocardial revascularization employing an elongated revascularization device. The revascularization may be performed from within the left ventricle or from the exterior of the heart. Various modifications to the present invention will become apparent to those skilled in the art from the foregoing description and accompanying drawings. Accordingly, the present invention is to be limited solely by the scope of the following claims.

What is claimed is:

1. A method of forming a revascularization channel in a desired region of a wall of a patient's heart, comprising:

| WATTAGE | DISTAL TIP TYPE | UNINSULATED LENGTH | PULSE DURATION | # OF PULSES |
| --- | --- | --- | --- | --- |
| 200 watts | Hollow | 0.05 inch | 100 msec | 6 |
| 200 watts | Hollow | 0.05 inch | 100 msec | 5 |
| 200 watts | Hollow | 0.05 inch | 100 msec | 5 |
| 200 watts | Hollow | 0.05 inch | 100 msec | 6 |
| 200 watts | Hollow | 0.05 inch | 100 msec | 5 |
| 200 watts | Hollow | 0.05 inch | 100 msec | 5 |
| 300 watts | Hollow | 0.05 inch | 100 msec | 3 |
| 300 watts | Hollow | 0.05 inch | 100 msec | 4 |
| 300 watts | Hollow | 0.05 inch | 100 msec | 4 |
| 300 watts | Hollow | 0.05 inch | 100 msec | 5 |
| 300 watts | Hollow | 0.05 inch | 100 msec | 4 |
| 300 watts | Hollow | 0.05 inch | 100 msec | 5 |
| 300 watts | Solid | 0.15 inch | 100 msec | 4 |
| 300 watts | Solid | 0.15 inch | 100 msec | 5 |
| 300 watts | Solid | 0.15 inch | 100 msec | 6 |
| 300 watts | Solid | 0.15 inch | 100 msec | 7 |
| 300 watts | Solid | 0.15 inch | 100 msec | 5 |
| 300 watts | Solid | 0.15 inch | 100 msec | 5 |

FIG. 10 illustrates an embodiment with a means to form a revascularization channel comprising a thermal ablation means 90 that is a channel forming surface. The shaft 91 generally includes two electrodes 92 that run the length of the shaft 91 and connect at the distal end of the device to a resistive themal probe 93. The proximal ends of the electrodes 92 are connected to a variable power supply (not shown) configured to supply sufficient current through the resistive thermal probe 93 to generate heat capable of a) providing an elongated shaft having proximal and distal ends and an RF energy emitter located at the distal end;

b) introducing the elongated shaft into the body of the patient and directing the RF energy emitter to the desired region of the heart wall wherein the revascularization channel is to be formed; and c) supplying RF energy to the RF energy emitter to form a revascularization channel in a myocardial layer of the patient's heart wall.

2. The method of claim 1 wherein the elongated shaft is a flexible intravascular shaft, further comprising the steps of:
   a) introducing the shaft into the patient's body by advancing the shaft through the patient's vasculature until a distal portion thereof is disposed within a chamber of the patient's heart defined by the wall;
   b) directing the RF energy emitter to the endocardial layer of the desired region of the wall; and
   c) supplying RF energy to the RF energy emitter to first remove tissue from an endocardial layer of the patient's heart wall when forming the revascularization channel.

3. The method of claim 1 wherein the elongated shaft is configured to be introduced through the patient's chest wall, further comprising the steps of:
   a) directing the RF energy emitter to the epicardial layer of the desired region of the wall; and
   b) supplying RF energy to the RF energy emitter to remove tissue sequentially from the epicardial layer, a myocardial layer and an endocardial layer to form the revascularization channel.

4. The method of claim 2 wherein the RF energy emitter is advanced through the endocardial layer at a first energy level and within the myocardial layer at a second energy level lower than the first energy level.

5. The method of claim 1 wherein the elongated shaft includes means for perfusing and aspirating the desired region of the heart wall, further comprising aspirating the removed tissue from the patient's heart.

6. The method of claim 1 wherein the RF energy emitter comprises a probe connected to a first and second electrode which extend the length of the elongated shaft, further comprising the step of supplying RF energy across the electrodes to form the revascularization channel.

7. The method of claim 6 wherein the revascularization channel is formed by supplying RF energy between about 30 MHZ to about 10 GHz across the electrodes.

8. A method of forming a revascularization channel in a desired region of a wall of a patient's heart, the wall having an inner endocardium layer, an outer epicardium layer and an intermediate myocardium layer between the endocardium and the epicardium layers, comprising:
   a) providing an elongated device having proximal and distal ends and a means to form a revascularization channel comprising radiofrequency ablation means located at the distal end;
   b) introducing the device into the body of the patient and directing the distal end of the device to the desired region of the wall wherein the revascularization channel is to be formed; and
   c) supplying radiofrequency energy to the radiofrequency ablation means to form a revascularization channel in the myocardium layer.

* * * * *